United States Patent [19]
Matsumoto et al.

[11] Patent Number: 6,045,541
[45] Date of Patent: Apr. 4, 2000

[54] DEVICE FOR TAKING UP FLUID

[75] Inventors: Toru Matsumoto; Narushi Ito, both of Tokyo, Japan

[73] Assignee: NEC Corporation, Tokyo, Japan

[21] Appl. No.: 09/017,555

[22] Filed: Feb. 3, 1998

[30] Foreign Application Priority Data

Feb. 4, 1997 [JP] Japan .................................... 9-021610

[51] Int. Cl.[7] ................ A61M 1/00; A61B 5/00
[52] U.S. Cl. ............ 604/313; 604/289; 600/573
[58] Field of Search ................ 604/289, 313–316, 604/19, 131, 181, 212; 600/573, 576, 577, 578

[56] References Cited

U.S. PATENT DOCUMENTS

| | | | |
|---|---|---|---|
| 4,151,832 | 5/1979 | Hamer | 128/765 |
| 4,190,060 | 2/1980 | Greenleaf et al. | 128/760 |
| 5,417,206 | 5/1995 | Kaneyoshi | 604/313 |
| 5,441,490 | 8/1995 | Svedman | 604/289 |
| 5,762,640 | 6/1998 | Kajiwara et al. | 604/313 |
| 5,782,871 | 7/1998 | Fujiwara et al. | 604/313 |
| 5,897,512 | 4/1999 | Zagame | 604/313 |

FOREIGN PATENT DOCUMENTS 5-172713  7/1993  Japan .

*Primary Examiner*—Corrine McDermott
*Assistant Examiner*—David J. Cho
*Attorney, Agent, or Firm*—Young & Thompson

[57] ABSTRACT

A device for taking up a fluid present on a flexible surface includes a support member and a fluid-passage member; the support member includes an opening portion having an end surface defining an abutment surface adapted to be held in abutment with the flexible surface; the fluid-passage member includes an aperture and is disposed within the opening portion of the support member; the fluid-passage member has an opening end defining an inlet, and is constructed to permit the fluid to flow thereinto by capillarity; the opening end having an end face is disposed inside with respect to the abutment surface of the support member and is positioned such that, when the abutment surface of the support member is brought into abutment with the flexible surface, only the fluid present thereon is brought into contact with the end face.

19 Claims, 6 Drawing Sheets

7: pressure-reducing suction port
1: tubular support member
2: fluid-passage member
5: skin
4: fluid
3: opening portion 4: fluid 4: fluid 4: fluid 1: tubular support member
16: fluid taking-up part
2: fluid-passage member
7: pressure-reducing suction port 15: fluid taking-up portion
1: tubular support member
2: fluid-passage member

DEVICE FOR TAKING UP FLUID

BACKGROUND ART

1. Field of the Invention

The present invention pertains to a device making it possible to conveniently take up or collect a fluid or liquid which is present on a flexible surface, and more particularly to a device for taking up a fluid or liquid present on an epithelium of an organism. The device of the invention is, in particular, intended to take up or sample sweat, secretion, tissue fluid, sucked exudate or the like exuded or secreted on the skin.

2. Related Art

A conventional device for taking up a body fluid generally has such a construction that blood, for example, is taken up by puncturing the skin with a hollow injection needle. In particular, the measurement of blood sugar for patients suffering from diabetes using an abbreviated blood sugar-measuring instrument is effected with the blood taken up by puncturing a lancet into the skin of a finger tip or the like of the patient. Inasmuch as the reduction of the quantity of blood required for the measurement, the miniaturization of the instrument as well as the simplification of the procedural method of use have been achieved by this abbreviated blood sugar-measuring instrument, it is now possible to effect such measurement outside hospitals, such as at home.

However, inasmuch as the sampling of blood, even of a small quantity, is required for the measurement of blood, danger to infection and mental burden caused by pain are accompanied for the patients.

In recent years, there is a demand on safer and easier procedures to solve these problems. As result, a method of taking up blood in a quantity of 1 microliter or less by utilizing a micro-machining technique or the like is proposed, and attention has been paid to body fluids other than blood, such as sweat, exudate or the like, as a fluid to be measured.

Such a body fluid can be taken up only in a small quantity of a microliter order, and vaporizes immediately when left on the skin. Therefore, it is necessary for a device of the type which takes up such a body fluid to have a function of taking up the body fluid as quickly and conveniently as possible.

A conventional device for taking up a body fluid present on the skin is described, for example, in Japanese Utility Model Application, Laid-Open No. Hei 1-49597, and is depicted in FIG. 8. This conventional device is constructed so as to take up a body fluid 29 into a fluid-reservoir 32 by sucking the skin 35 under pressure through a sucking opening 36. In this device, a spacer 26 is interposed between the sucking opening 36 and the skin surface in order to prevent the intimate contact of the sucking opening 36 against the skin 35, and the delivery of the body fluid 29 towards the outside of the device is conducted by closing an electromagnetic valve 33 arranged between the fluid-reservoir 32 and the sucking opening 36 and subsequently opening an openable lid 27.

However, the conventional device depicted in FIG. 8 has the following disadvantages:

First, the operation of the device requires a considerable number of procedural steps, resulting in inconvenience in manipulation. More specifically, this device requires an operation of taking up the body fluid into the fluid-reservoir by suction, an operation of closing the electromagnetic valve and an operation of delivering the body fluid by opening the lid.

Second, since the device uses, for example, an electromagnetic valve, the number of parts required for the assembly is great, resulting in an increased manufacturing cost. As a result, the device cannot be of a disposable type. Furthermore, since it cannot be of a disposable type, a very laborious operation of washing the device is additionally required.

Third, it is not possible to reduce dead volume. More specifically, since the device includes an openable valve, such as an electromagnetic valve, at a fluid passage between the skin sucking opening and the fluid-reservoir, the dead volume or space is large and not negligible for the delivery of a small quantity of fluid. In addition, since the body fluid adheres to the wall surface of the fluid-reservoir, it is not possible to take out the taken-up body fluid completely.

SUMMARY OF THE INVENTION

It is therefore a primary object of the present invention to provide a device making it possible to take up a fluid or liquid present on a flexible surface, and in particular a body fluid present in a small quantity on a surface of an organism such as skin surface.

Another object of the invention is to provide a fluid-taking up device, whose taking-up part is very simple in structure, and which enables the substantial reduction of the manufacturing cost.

A further object of the invention is to provide a fluid-taking up device which enables an efficient use of the taken-up fluid, without any substantial loss, for desired purposes.

According to the present invention, there is provided a device for taking up a fluid present on a flexible surface, comprising: a support member including an opening portion having an end surface defining an abutment surface adapted to be held in abutment with the flexible surface; and a fluid-passage member including an aperture and disposed within the opening portion of the support member, the fluid-passage member including an opening end defining an inlet and being constructed to permit the fluid to flow thereinto by capillarity, the opening end having an end face being disposed inside with respect to the abutment surface of the support member and positioned such that, when the abutment surface of the support member is brought into abutment with the flexible surface, only the fluid present thereon is brought into contact with the end face.

In the device as constructed above, a fluid, such as a body fluid present on the epithelium of an organism, is spontaneously taken up into the fluid-passage member by capillarity or capillary phenomena. For example, when the entire end surface of the opening portion of the support member is brought into abutting contact with the epithelium, the epithelium is more or less raised into the opening portion of the support member, and as the fluid present on the epithelium is brought into contact with the inlet opening end of the fluid-passage member, the body fluid is taken up into the fluid-passage member by capillarity. The body fluid thus taken up can be kept within the fluid-passage member of the device by surface tension even after the device is moved apart from the epithelium. The body fluid thus taken up can be delivered for example to an instrument for chemical analysis, where the chemical analysis is effected easily. Accordingly, the device in accordance with the present invention is advantageous in that its operation is very easy, the number of assembly parts is small, the structure is simple, the manufacturing cost is low, and it is suitable for use as a device of a disposable type. In addition, if the device is constructed such that the fluid on the epithelium contacts only the inlet opening end of the fluid-passage member, even a small quantity of fluid can be taken up without any loss. Furthermore, the device may utilize the fluid-passage member which consists of a pore structure or capillary structure and achieves the minimum volumetric capacity required for the fluid sampling operation. Consequently, the dead space within the device can be minimized, and it is possible to utilize the entire quantity of the taken-up fluid for desired purposes. Moreover, if a fluid taking-up portion provided on the fluid passage member is attached to the support member so as to be releasable therefrom, and if the fluid taking-up portion is released after the collection of the fluid and is used as a sample for instruments for analysis, it will be possible to use the taken-up fluid entirely. Additionally, if the fluid taking-up portion is constructed to have a structure or configuration suitable for delivery or preservation, it is possible to detach and deliver or preserve the same.

In the device in accordance with the present invention, even when the epithelium is not raised into the opening portion of the support member, it is possible to take up the fluid present on the epithelium. However, the formation of a convex surface by raising the epithelium and the positioning of the convex surface in contact with the fluid enable a more efficient contact between the inlet of the fluid-passage member and the fluid as well as the collection of the fluid by the action of capillarity. From this viewpoint, the device may be constructed such that it is possible to reduce the pressure within the opening portion of the support member, and it is possible to raise the skin more effectively by reducing the pressure while holding the opening portion in abutting contact with the epithelium. This structure is particularly advantageous in the cases where the opening area for the opening portion of the support member is small, and where the pressing contact of the support member is not adequate to obtain a sufficient raised state of the skin. Moreover, the formation of the raised skin is also effective in the case of taking up a fluid present in the recesses at the skin, for example exudate within wound.

Any construction may be used as the pressure-reducible construction, provided that it is possible to close the opening portion in an airtight manner while pressing the entire end surface of the opening portion, which defines an abutment surface of the support member against the skin, towards the skin, and reduce the pressure in the opening portion by any suitable means. Thus, the pressure-reducing means may be provided integrally with the support member, or may be constructed so as to be releasable therefrom. If the pressure-reducing means is constructed to be releasable, that part other than the pressure-reducing means can be constructed to be disposable. Therefore, the problem of infection caused by the taken-up fluid in the case where the same pressure-reducing means is repeatedly used can be avoided, and it becomes possible to take up any fluid at a reduced cost.

Furthermore, if a suitable sensor is mounted within the fluid-passage member, it may be possible to detect the completion of the fluid taking-up operation based on its detection signal, or to conduct an analysis for a chemical composition of the taken-up fluid.

In the device in accordance with the present invention, it may be possible to arrange a plurality of fluid-passage members in the opening portion of the support member. With this construction, it is possible to take up the same fluid into different fluid-passage members, or to take up several fluids present on different portions of the skin into respective fluid-passage members. Furthermore, it is possible to use different fluids for different purposes. For example, it is possible to use the samples for the analysis of various items by taking up the same fluid into the plural fluid-passage members. Moreover, preservation may be required for a certain analytical item, and in such a case, an anti-glycolysis agent, an antiseptic or the like may be incorporated in a dried state in advance within the fluid-passage member to ensure the stable preservation of the fluid after the collection. In addition, if a plurality of sensors having different functions are provided for the plural fluid-passage members, respectively, and if the same fluid is taken up into those fluid-passage members, it is possible to measure a plurality of chemical components simultaneously.

Furthermore, in the device in accordance with the present invention, inasmuch as the fluid-passage member is disposed inside the opening portion of the support member, it may be possible to attach a protection cover for the opening portion of the support member to avoid any damage. Moreover, even in the state where the opening portion of the support member is opened during the collection operation of fluid, the fluid-passage member can be placed on a suitable planar surface without causing any pollution and damage to the fluid-passage member.

Thus, the device in accordance with the present invention is very suitable to take up fluid or liquid present on the epithelium, and in particular an aqueous body fluid exuded or secreted on the skin, such as sweat, secretion, tissue fluid, sucked exudate or the like.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE PREFERRED EMBODIMENTS OF THE INVENTION

Figure 1:
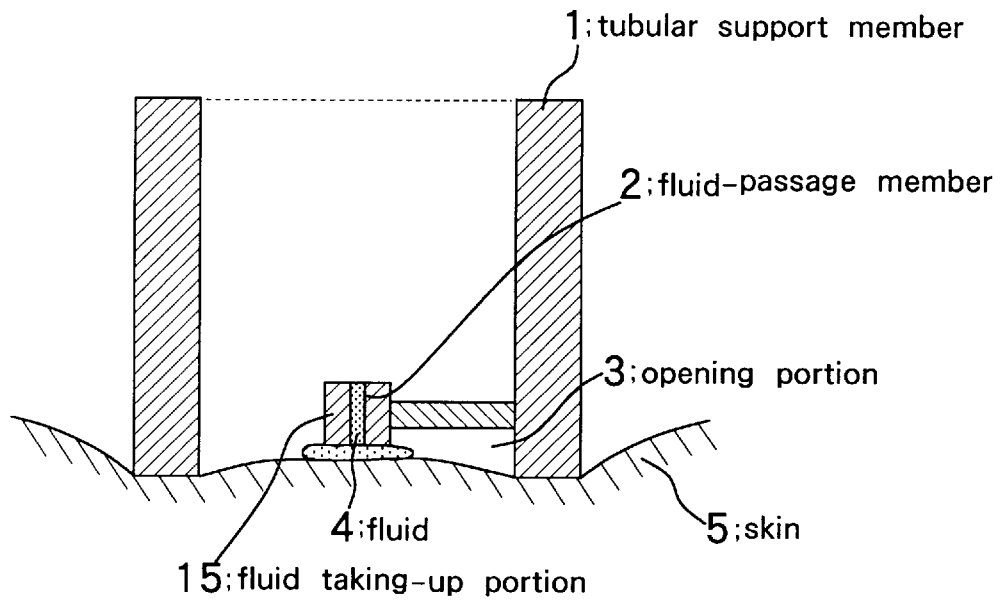
FIG. 1 is a cross-sectional view showing a fluid-taking up device in accordance with a first embodiment of the present invention.

FIG. 1 is a cross sectional view depicting a device for taking up fluid in accordance with a first embodiment of the present invention.

The device comprises a hollow and tubular support member 1 having opening opposite ends, and a fluid taking-up portion or part 15 including a fluid-passage member 2 and disposed so as to be displaced inwardly from the end face of one of the opening portions of the support member 1.

In the device illustrated, the opening end surface of the opening portion 3 serving as an abutment surface against the skin 5 is pressed against the skin surface on which a fluid or liquid 4 to be taken up is present, the surface of the skin 5 is raised into the opening portion 3. Then, the fluid 4 present on the skin 5 is brought into contact only with the end face of the inlet opening end of the fluid-passage member 2, to be taken up spontaneously by capillarity into the fluid-passage member 2.

The tubular support member 1 can be formed of any material, provided that it has such a mechanical strength or structure that the fluid-passage member 2 can be kept in a desired position within the opening portion. In particular, materials having excellent water proof and/or chemical proof properties and/or workability are preferable. For example, a synthetic resin such as ABS resin, polycarbonate or the like, which may be suitable for an integral molding by the use of die assembly, can be mentioned.

The fluid-passage member 2 may be constructed so that fluid taken up by capillarity into the inlet can flow therethrough, and that it has a volumetric capacity enabling the collection of a sufficient quantity of fluid present on the skin. Since the capillarity depends primarily on the wettability of the fluid with the material constituting the inner peripheral surface of the tubing or the pore constituting the capillary, it is possible to construct the fluid-passage member so as to have an inner peripheral surface formed of a material having a hydrophilic property and define a cavity or void communicated with the outside through at least two opening portions, in order to take up a desired quantity of fluid. In the foregoing, the fluid-passage member may be of a structure having a single passage or a structure where a number of small chambers are successively communicated with each other. In view of the workability as well as the manipulative easiness of taking out the fluid after the collection, a linear passage as shown in FIG. 1 is suitable for the fluid-passage member. As a material for forming this fluid-passage member, various synthetic resins as well as silicon compounds such as ceramics, glass or the like are usable because they make it possible to form a hydrophilic inner wall surface and permit an integral molding. Furthermore, even a hydrophobic material may be used if it is possible to treat the inner wall surface to be hydrophilic after the formation of the fluid-passage member. Such treatments suitably utilized involve treatments with silane coupling agents or the like. Moreover, the cross-section of the fluid-passage member may be of an arbitrary shape, such as circle, triangle, square, rectangle, irregular shapes or the like, provided that it ensures capillarity.

The opening area of the opening portion 3 of the support member 1 may be selected while considering the surface area of the skin surface at which the fluid to be taken up is present as well as the manipulative performance of the device per se. In consideration of versatility for general or universal uses, the diameter (inner diameter) can be chosen from the range of from 1 mm to 80 mm. Furthermore, the configurations of the opening portion 3 of the support member 1 and the support member 1 per se will not be limited to a shape of circular cross-section as illustrated, but may be of various cross-sectional shapes such as triangle, square, rectangle, polygon such as pentagon, elliptical or the like, and may also be provided with different cross-sections in its axial direction. In consideration of the workability and handling easiness (such as positioning from the above), the tubular structure as shown in FIG. 1 is particularly preferable.

The configuration and size of the fluid taking-up portion having the fluid passage member 2 are not restricted to those shown in FIG. 1 either, provided that they permit the arrangement of the fluid-passage member in position.

In the foregoing, the size of the part having the fluid passage member 2 should be at least smaller than the inner diameter of the opening portion 3, and the upper and lower opening portions of the tubular support member 1 should be communicated with other parts outside the fluid-passage member 2.

Furthermore, the distance between the end surface of the opening portion 3 and the inlet of the fluid-passage member 2 can be chosen while considering the size of the opening portion 3 and the elasticity of the skin part on which the device is applied. For example, it may be chosen from the range of 0.1 mm to 40 mm.

Moreover, the connection of the fluid taking-up portion having the fluid-passage member 2 and the tubular support member 1 may be of an arbitrary construction, and is not restricted to that of FIG. 1, in which they are secured to each other by a single rod-like member.

Furthermore, it is possible to construct the fluid taking-up portion having the fluid-passage member 2 so as to be releasable from the tubular support member 1. With this construction, it is possible to render such a part disposable. This detachable construction will also be applied to the embodiments as will be described later.

As compared with the conventional device, the device of FIG. 1 is advantageous in that the constituting components are extremely simplified, the reduction of the manufacturing cost is easy, and it can be suitably used as a disposable type. In addition, it is possible to take up the fluid only by a simple operation to press the device against the skin, resulting in an improved operability. Furthermore, inasmuch as the fluid on the skin contacts only the opening face of the inlet of the fluid-passage member 2, it is possible to take up a fluid even in a small quantity without any loss.

Moreover, in the device of FIG. 1, the upper opening portion of the tubular support member 1 is in an opened state. However, it may be possible to add a covering to cover this opening portion. Additionally, it is possible to add a supplemental structure such as a handle to the tubular support member 1 in an integral or releasable manner in order to further improve its handling performance.

The fluid taken into the fluid-passage member 2 may be taken out by contacting the same with a water-absorbing material or by exerting pressure into the fluid-passage member 2.

Figure 2:
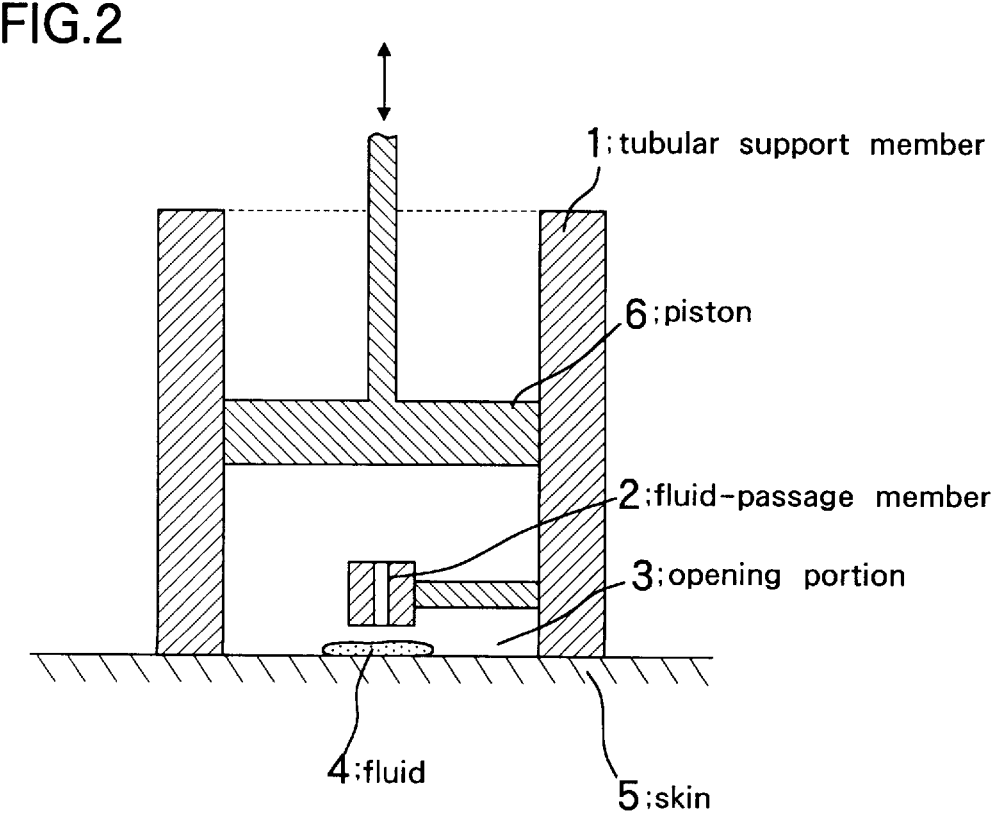
FIG. 2 is a view similar to FIG. 1, but showing a fluid-taking up device in accordance with a second embodiment of the present invention.

FIG. 2 is a cross-sectional view showing a device of the invention in accordance with a second embodiment. This device has a structure that in the device of FIG. 1, a pressure-reducing means including a piston 6 is further added, the piston 6 dividing the inside of the tubular support member 1 into the region which includes the upper opening portion and the region which includes the lower opening region. This piston 6 is disposed in the tubular support member for sliding movement therealong. Thus, when the piston 6 is caused to move upwards while pressing the opening portion 3 against the skin 5, the volume of the closed space defined by the inner wall surface of the tubular support member 1, the surface of the skin 5 and the lower end face of the piston 6 is enlarged to produce a reduced pressure therein, to thereby raise the surface of the skin 5 into the tubular support member 1 and to bring the fluid 4 into contact with the inlet of the fluid-passage member 2. This construction is advantageous in the case where the lower opening portion 3 is small, or where a sufficient deformation (raise) of the skin cannot be obtained by the urging of the tubular support member thereagainst. With the provision of such a pressure-reducing means, it is possible to render the diameter of the opening portion small to about 1 mm, and to broaden the applicable ranges to the skin having different deformability (elasticity). For example, if it is not necessary to use the pressure-reducing means, the device may be operated without it, and the pressure-reducing means may be activated only when it is necessary to do so.

Figure 3:
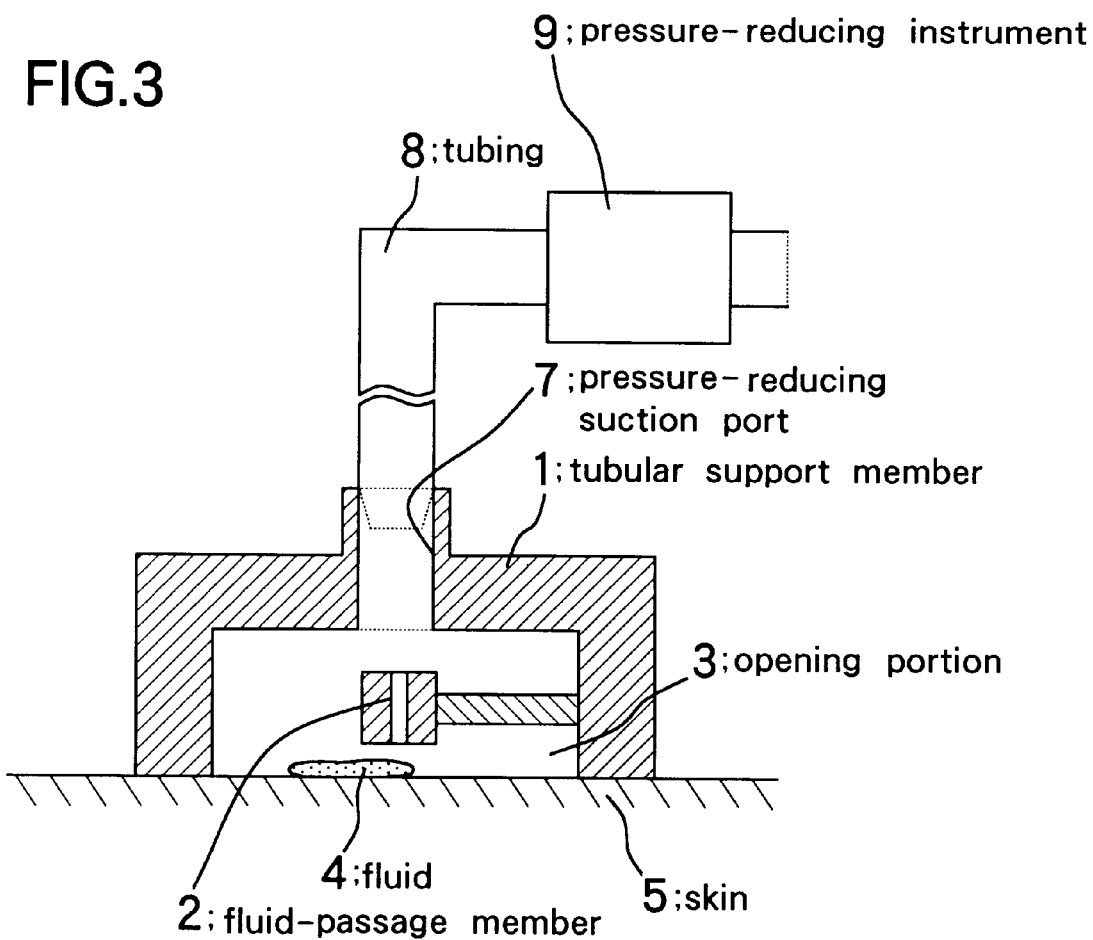
FIG. 3 is a view similar to FIG. 1, but showing a fluid-taking up device in accordance with a third embodiment of the present invention.

FIG. 3 is a cross-sectional view showing a device of the invention in accordance with a third embodiment. This device has a structure that in the device of FIG. 1, a pressure-reducing suction port 7 is added at the upper portion of the tubular support member 1. This suction port 7 enables the connection of a pressure-reducing instrument 9 through a tubing 8, and when the pressure-reducing instrument 9 is actuated while pressing the end surface of the lower opening portion 3 of the tubular support member 1 entirely against the surface of the skin 5, it is possible to obtain a raise of the skin as is the case with the device of FIG. 2. As the pressure-reducing instrument 9, an electrically-driven suction pump, a manual suction pump utilizing rubber, spring or the like, a suction unit employing a cylinder and piston assembly can be mentioned.

In the device of FIG. 3, the pressure-reducing suction port 7 and the tubing 8 maybe constructed to be integral, or constructed such that the tubing 8 is detachable from the suction port 7. In the case of the detachable construction, it is possible to construct the body portion of the device so as to disposable, rendering it possible to take up fluid safely at a reduced cost. In the case where an integral construction is chosen, it is necessary to add a mechanism to restore the pressure-reduced inside of the tubular support member to an atmospheric pressure.

Figure 4:
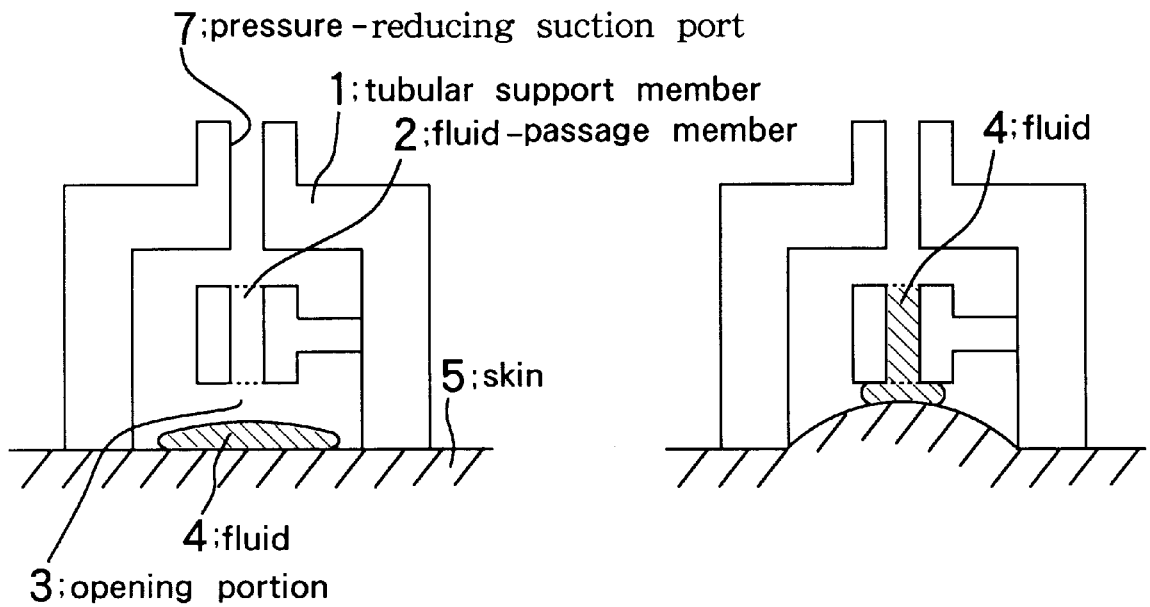
FIGS. 4(a) to 4(d) are schematic views for explaining the operation and function of the device of FIG. 3.
Figure 4:
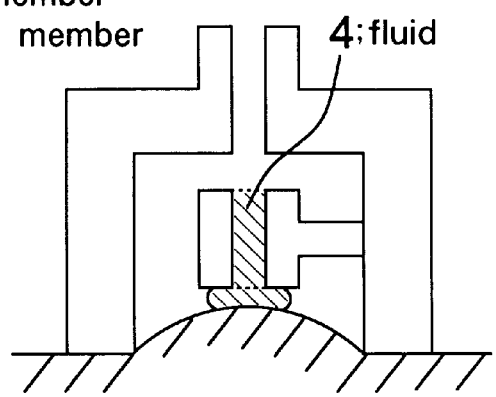
Figure 4:
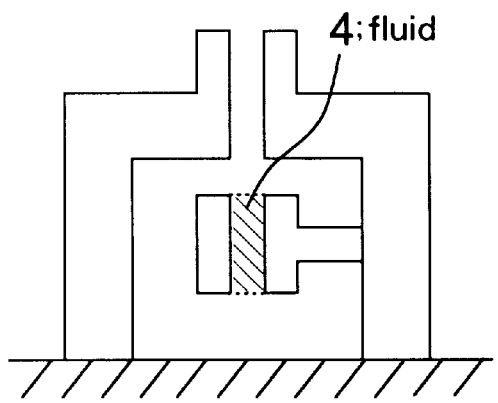
Figure 4:
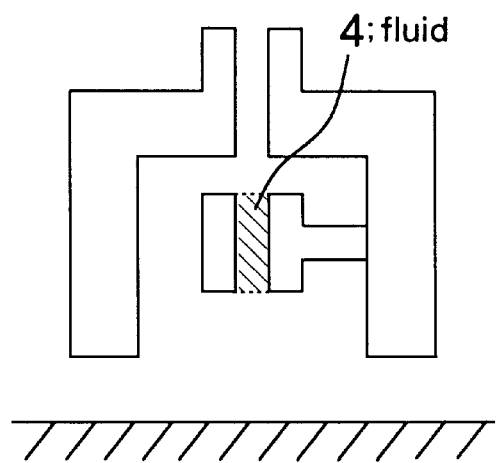

The method of use for the device illustrated in FIG. 3 will be shown in FIG. 4. First, as shown in FIG. 4(a), the end surface of the lower opening portion 3 of the tubular support member 1 is entirely urged against a prescribed part of the skin 5. Thereafter, as shown in FIG. 4(b), the pressure reducing instrument (not shown) is activated to effect the suction operation to raise the skin 5, and to bring the fluid 4 into contact with the inlet of the fluid-passage member 2 to take up the fluid 4 into the fluid-passage member 2 by capillarity. In this state, as shown in FIG. 4(c), the suction opening 7 is opened to restore the inside pressure to an atmospheric pressure, and as shown in FIG. 4(d), the device is released apart from the skin 5 to complete the collection operation.

Figure 5:
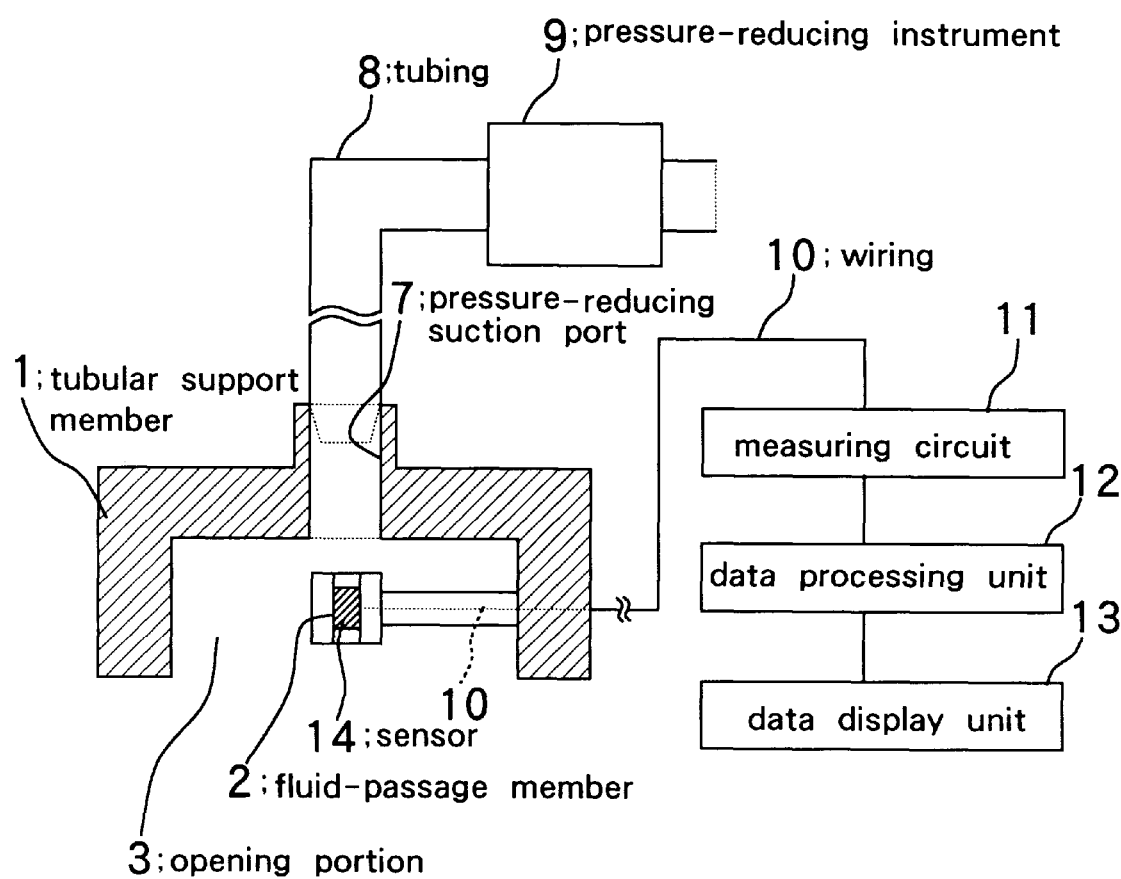
FIG. 5 is a schematic cross-sectional view showing a fluid-taking up device in accordance with a fourth embodiment of the present invention.

FIG. 5 is a cross-sectional view showing a fluid taking-up device in accordance with a fourth embodiment of the present invention. The device differs from that of FIG. 3 only in that it comprises a sensor 14 disposed in the fluid-passage member 2 and a means for outputting the signal obtained from the sensor 14. In this device, the outputting, recording and analysis of the detection signals obtained by the sensor 14 may be conducted using a system in which the sensor 14, a measuring circuit 11, a data processing unit 12 and a data display unit 13 are connected by wiring 10. In the foregoing, the sensor as well as various equipment to be connected to the sensor may be selected arbitrarily so as to be suited to the present purposes. For example, in the case where the sensor 4 is a sensor for electric conductivity, the electro-conductivity changes when the fluid is taken up in the fluid-passage member 2 and the fluid contacts the sensor, so that it is possible to detect the completion of collection more precisely. Furthermore, in the case where the sensor 14 is a chemical sensor, in addition to the detection of the completion of the collection of the fluid, it is possible to effect a qualitative and quantitative analysis for a chemical substance present in the fluid. In the foregoing, as a chemical sensor, an electrochemical sensor using a transducer such as amperometric system or potentiometric system, a photosensor such as an optical fiber system detecting variations in coloring matter and fluorescence or optical conductive passage may be used. Furthermore, it is possible to use an enzyme sensor in which an enzyme is fixed to an electrochemical sensor or an ion sensor in which various ion-sensitive membranes are combined. As specific examples for the enzyme sensor, a sensor in which an enzyme which acts on lactic acid, glucose, galactose, sucrose, ethanol, methanol, starch, uric acid, pyruvic acid, creatine, creatinine, 3-hydroxybutyric acid, bilirubin, oxalic acid, amino acid, monoamine, cholesterol, choline or the like is fixed to enable the qualitative or quantitative analysis of these substances can be mentioned. As a sensor of a potentiometric type, an ion-sensitive field effect transistor type can be used to measure ionic components obtained from hydrogen (pH), sodium, potassium, chlorine, calcium, lithium carbonate, salicylic acid, bromides, procaine amides, bretylium, disopyramide or the like.

Figure 6:
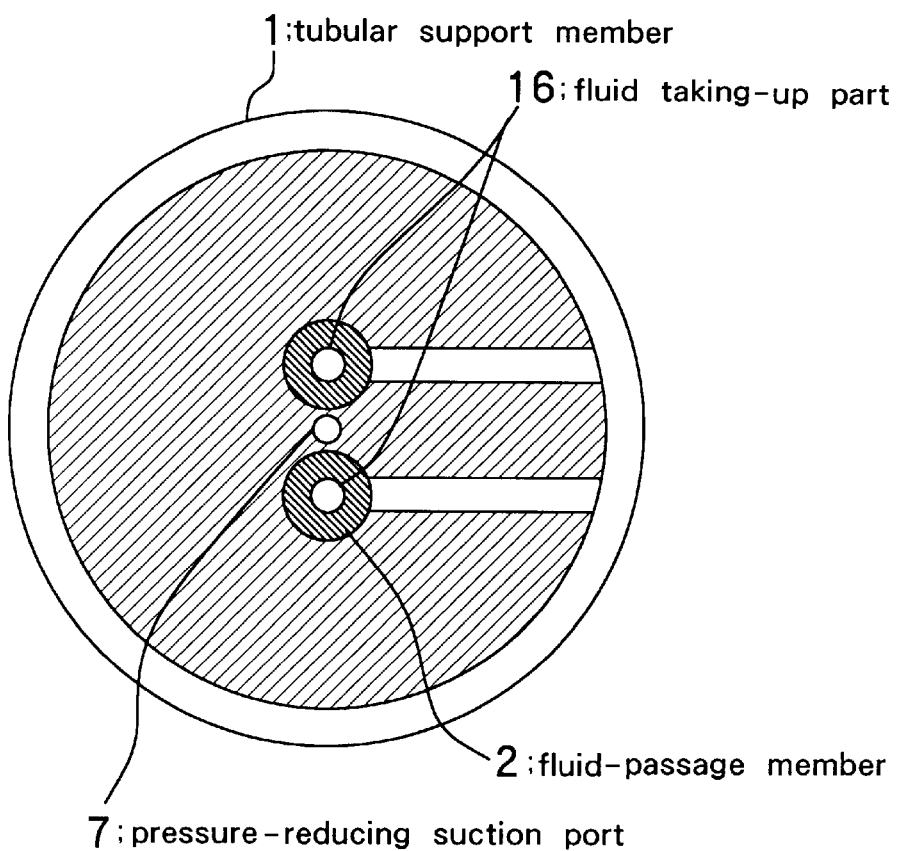
FIG. 6 is an end view showing a fluid-taking up device in accordance with a fifth embodiment of the present invention.

FIG. 6 is a bottom view as seen from the lower opening portion 3 of the tubular support member 1, and shows a device in accordance with a fifth embodiment of the present invention. This device differs from that of FIG. 3 or FIG. 5 only in that two fluid taking-up parts 16 each having a fluid-passage member 2 are disposed in the lower opening portion 3. It is needless to say that this construction can also be applied to the devices of other construction, such as the devices of the construction of FIG. 1 or FIG. 7. Furthermore, the fluid-passage members to be arranged in one opening portion may be three or more, and a plurality of fluid-passage members may be provided in a single fluid taking-up portion. With this construction, since a plurality of fluid-passage members are provided, if the same fluid is taken up into these fluid-passage members, it is possible to use the fluid for more than two uses. In this case, if an anti-glycolysis agent, a chelating agent, an antiseptic or the like are filled in a dry state in the fluid-passage member, it is possible to automatically obtain an effect similar to that obtained by adding such agents to the taken up fluid, and it is thus possible to preserve the taken-up fluid stably for the desired analytical purposes.

Figure 7:
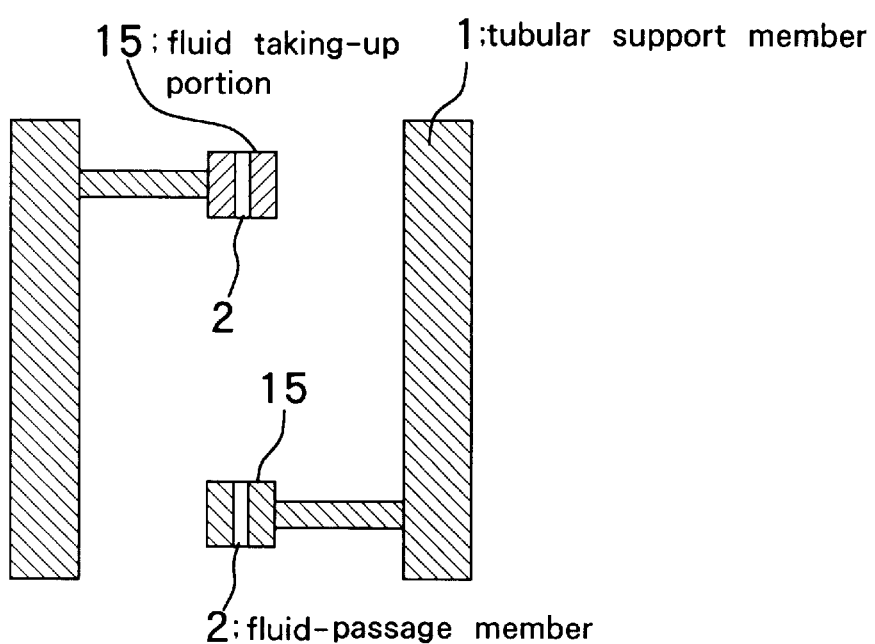
FIG. 7 is a cross-sectional view showing a fluid-taking up device in accordance with a sixth embodiment of the present invention.
Figure 8:
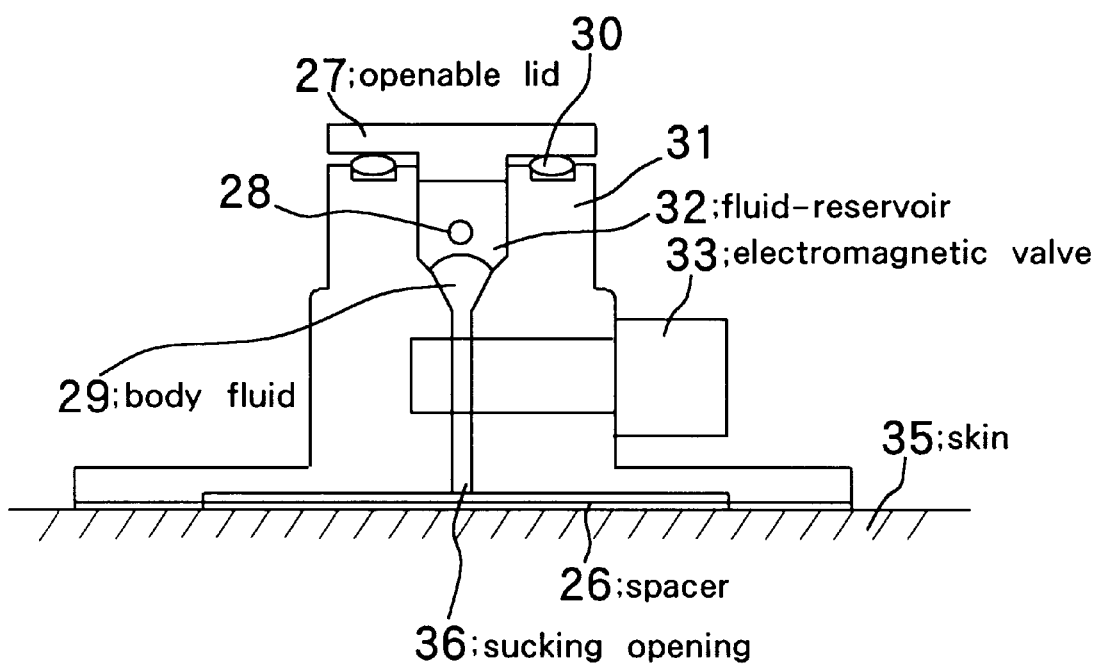
FIG. 8 is a cross-sectional view showing a conventional fluid-taking up device.

FIG. 7 depicts a device in accordance with a sixth embodiment of the present invention. This device differs from that of FIG. 1 in that an additional fluid taking-up portion 15 is further provided in the upper opening end of the tubular support member 1. With these two fluid taking-up portions 15, it is possible to take up fluid from different parts of the skin.

As described above, in the device in accordance with the present invention, the flexibility inherent in the skin is positively utilized to bring the fluid on the skin into contact with the inlet of the fluid-passage member, and the fluid-passage member spontaneously takes up the fluid by capillarity. Accordingly, it is possible to take up a small quantity of fluid by a convenient procedural operation in a short time without any substantial loss. Furthermore, inasmuch as the device is simple in structure, that part of the device which contacts the fluid can easily be constructed to be disposable. In addition, it is possible to effect the collection of the fluid and the measurement of a specific component at a reduced cost.

The present invention will be explained in more detail by way of the following examples.

EXAMPLE 1

Five kinds of devices for taking up fluid having a construction as shown in FIG. 1 were prepared by arranging fluid-taking up portions at one of the opening portions of a tubular support member of vinyl chloride having an outer diameter of 28 mm and an inner diameter of 20 mm while varying the distance between the end surface of the opening portion and the inlet of the fluid-passage member. The fluid-passage member was constructed using a capillary glass tube (5 mm in length and about 4 $\mu$l of volumetric capacity) having an inner diameter of 1.0 mm (outer diameter of 1.2 mm) and opening at opposite ends, and the support member and the glass tube were connected by using a flexible base member of polyimide. In the foregoing, the support member had a groove formed therein so that the flexible base member can be fit at an arbitrary position.

The test was conducted using these five fluid-taking up devices independently. More specifically, each device was pressed against the skin of the forearm of a subject having a small quantity of a fluid (about 50 $\mu$l) so that an equal load is exerted thereon, and the fluid taking-up performance was evaluated by the visual observation as to whether the fluid was taken up into the fluid-passage member. The results are set forth in Table 1. In this table, ○ means that the fluid was successfully taken up, whereas × means that the fluid was not taken up.

TABLE 1

| Subject | Distance between the opening end surface of the support member and the fluid-passage member inlet (mm) | | | | |
| --- | --- | --- | --- | --- | --- |
| | 0 | 2.5 | 5.0 | 7.5 | 10.0 |
| A | X | ○ | ○ | ○ | ○ |
| B | X | ○ | ○ | X | X |
| C | ○ | ○ | ○ | ○ | ○ |
| D | X | ○ | ○ | ○ | X |

As shown in Table 1, in some of the cases where the distance between the end surface of the opening portion of the tubular support member 1 and the inlet of the fluid-passage member is zero, that is, both are located on the same plane, no fluid was taken up because the opening of the inlet of the fluid-passage member was closed by the skin surface per se when brought into contact with the fluid on the skin. On the other hand, in some of the cases where the distance was set unduly great, no fluid was taken up either. However, these results were due to the difference in the flexibility of the skin between individuals, and when a load was further exerted on the skin surface, the fluid was successfully taken up. These results show that when the inlet opening end of the fluid-passage member is situated above (inside) the end surface of the opening portion of the support member, the fluid can be taken up well.

EXAMPLE 2

The same procedures as in Example 1 were taken, except for the formation of the tubular support member in conformity with FIG. 3 by providing a lid having an evacuation port at the upper opening portion of the support member, to thereby prepare five kinds of devices for taking up fluid.

The test was conducted using these five fluid-taking up devices independently. More specifically, each device was pressed against the skin of the forearm of a subject having a small quantity of a fluid (about 50 $\mu$l) so that an equal load is exerted thereon, and the inside of the support member was slowly evacuated through the pressure-reducing sucking port to 0.5 atm, and was recovered to the atmospheric pressure. Thus, it was evaluated by the visual observation as to whether the fluid was taken up into the fluid-passage member. The results are set forth in Table 2. In this table, ○ means that the fluid was successfully taken up, whereas × means that the fluid was not taken up.

TABLE 2

| Subject | Distance between the opening end surface of the support member and the fluid-passage member inlet (mm) | | | | |
| --- | --- | --- | --- | --- | --- |
| | 0 | 2.5 | 5.0 | 7.5 | 10.0 |
| A | X | ○ | ○ | ○ | ○ |
| B | X | ○ | ○ | ○ | ○ |
| C | X | ○ | ○ | ○ | ○ |
| D | X | ○ | ○ | ○ | ○ |

The results shown in Table 2 show that when the opening end of the inlet of the fluid-passage member is disposed above (inside) the end surface of the opening portion of the support member and the pressure reducing operation is also effected, the skin is effectively deformed convexly, so that the fluid on the skin can be brought into contact with the inlet of the fluid-passage member to be well taken up, and that the fluid remains in the fluid-passage member even after the evacuation is ceased. Furthermore it is also shown that it is possible to improve the variance caused by the difference in flexibility of the skin between individuals.

EXAMPLE 3

After a groove of a predetermined width and depth (width=depth) was formed in a glass base plate by cutting with a dicing saw and grinding, a planar glass plate was bonded thereon as a covering to form a chip having a linear fluid-passage of 10 mm long having an opening of a square cross-section. As depicted in Table 3, six kinds of these chips which had different side lengths for the opening were prepared. As a fluid taking-up portion, each chip was arranged in one of the opening portions of the tubular support member of transparent acrylic resin having an outer diameter of 24 mm and an inner diameter of 20 mm to prepare six kinds of fluid taking-up devices having a structure as illustrated in FIG. 1. In this example, the distance between the inlet (lower opening end) of the fluid-passage member and the end surface of the opening portion of the support member was commonly set to 5 mm for all the devices.

The test was conducted using these six fluid-taking up devices independently. More specifically, each device was pressed against the same portion of the skin of the same subject, and a droplet (an aqueous solution containing 5% by weight of albumin) was taken up. Further, in the case where the droplet was taken up, the time period required up to the completion of the collection was determined by visually observing the rise of the fluid level from the point at which the fluid contacted the opening end of the fluid-passage member. The results are set forth in Table 3.

TABLE 3

| Length of one side of cross-section and volume of the fluid-passage member | | Taken up or not | Time required for taking up (sec) |
|---|---|---|---|
| Length (mm) | Volume (µl) | | |
| 0.5 | 2.5 | Taken up | 1.0 or less |
| 0.6 | 3.6 | Taken up | 1.4 |
| 0.7 | 4.9 | Taken up | 1.7 |
| 0.8 | 5.4 | Taken up | 2.5 |
| 1.0 | 10.0 | Taken up | 2.9 |
| 1.4 | 19.6 | Not taken up | — |

The results set forth in Table 3 show that even in the case where the cross-sectional configuration of the fluid-passage member (inclusive of opening configuration) is set to a square, fluid can be taken up by capillarity. In addition, it is possible to complete the collection of the fluid within 3 seconds by selecting an appropriate size of the opening.

EXAMPLE 4

After having provided on a silicon base plate a mask pattern in conformity with the arrangement of a desired groove, an isotropic etching was effected thereon to obtain a grooved base plate having parallel-arranged linear grooves of different widths (the width at the surface of the base plate: 50, 100, 200, 300, 400 µm; depth: 40 µm) and of a semi-cylindrical cross-sectional shape (the bottom of the groove is of a concave shape). Further, a glass base plate having a planar surface was bonded to the grooved silicon base plate, and base members having fluid-passages of different widths with undefined cross-sections were obtained.

As a pseudo-serum, an aqueous solution of 5% by weight of albumin was prepared, and the end face at which each fluid-passage is opening was brought into contact with this fluid. Thus, it was determined as to whether the fluid-passage member was filled with the fluid by observing the rise of the fluid level visually. Table 4 shows the results as to whether the fluid-passage member was filled with the fluid over the entire length, and the time required for taking up the fluid when taken up.

TABLE 4

| Width of the fluid-passage and its volumetric capacity | | Taken up or not | Time required for taking up (sec) |
|---|---|---|---|
| Width (µm) | Volume (µl) | | |
| 50 | 0.1 | Taken up | 1.0 or less |
| 100 | 0.3 | Taken up | 1.0 or less |
| 200 | 1.0 | Taken up | 1.0 or less |
| 300 | 2.3 | Taken up | 1.0 or less |
| 400 | 4.1 | Taken up | 1.0 or less |

The results set forth in Table 4 show that even in the case where the fluid-passage members are those which have the groove width of 400 µm or less and an irregular cross-section having volumetric capacity of 4.1 µl or less, it is possible to take up fluid in a short time of 1.0 second or less.

EXAMPLE 5

After having provided on a silicon base plate a mask pattern in conformity with the arrangement of a desired groove, an isotropic etching was effected thereon to obtain a grooved base plate having parallel-arranged grooves of different widths (the width at the surface portion: 50, 100, 200, 300, 400 µm; depth: 40 µm) and of a V-shaped cross-section. Further, after a glass base plate having a planar surface was bonded to the grooved silicon base plate, they were cut at a predetermined position, and base members having fluid-passage members of different widths with undefined cross-sections were thus obtained.

The same test of taking up fluid as in Example 4 was effected with respect to the base members thus obtained. The results obtained are set forth in Table 5.

TABLE 5

| Width of the fluid-passage (µm) | Taken up or not | Time required for taking up (sec) |
|---|---|---|
| 50 | Taken up | 1.0 or less |
| 100 | Taken up | 1.0 or less |
| 200 | Taken up | 1.0 or less |
| 300 | Taken up | 1.0 or less |
| 400 | Taken up | 1.0 or less |

The results set forth in Table 5 show that even in the case where the fluid-passage member are those of triangular cross-sections which have a bottom length of 400 µm or less, it is possible to take up fluid in a short time of 1.0 second or less.

EXAMPLE 6

A plurality of fluid taking-up portions having fluid-passage members having an inner diameter of 1.0 mm and a length of 10 mm (volumetric capacity of about 8 µl) were prepared using ABS resin. With respect to each of the fluid-passage members thus obtained, performance of taking up fluid was tested before and after the hydrophilic property-imparting treatment using an aqueous solution of 1% by weight of γ-aminopropyl triethoxysilane while using an aqueous solution of 5% by weight of albumin as a pseudo-serum. The inlet of the fluid-passage member was left in contact with the fluid for a while, and the volumetric capacity of the fluid taken up into the fluid-passage member when released from the fluid was measured by measuring the distance of the fluid level elevated. The results obtained are shown in Table 6.

TABLE 6

| Fluid-passage member | Before hydrophilic treatment | After hydrophilic treatment |
|---|---|---|
| A | Taken up partly (about 2 µl) | Taken up entirely |
| B | Taken up partly (about 5 µl) | Taken up entirely |
| C | Taken up partly (about 4 µl) | Taken up entirely |
| D | Taken up partly (about 2 µl) | Taken up entirely |

The results set forth in Table 6 show that even a hydrophobic material such as ABS resin can be utilized as a constructing member for the fluid taking-up portion if it is subjected to an appropriate hydrophilic treatment before use. As a result, mass production using an inexpensive material is possible.

EXAMPLE 7

A planar glass plate was bonded to a glass base member having linear grooves of rectangular cross-section of a prescribed size formed therein, the planar glass plate having a glucose sensor (width: 0.8 mm; length: 2.2 mm) wherein glucose oxidase was fixed on two platinum electrode and silver/silver chloride electrode so as to correspond to the grooves of the base plate. Thus, four fluid taking-up portions (length: 5 mm, side: 1.6 mm, width: 6 mm) each having a glucose sensor at a sealing portion thereof were obtained. In the foregoing, with respect to the fluid-passages, depth (0.5 mm) and length (5 mm) were set identical, and the width was varied to 1.0 mm, 2.0 mm, 3.0 mm and 4.0 mm (volume: 2.5, 5.0, 7.5 and 10.0 $\mu$l).

Using respective fluid taking-up portions independently, the fabrication procedures as in Example 1 were repeated to obtain fluid taking-up devices having a structure as shown in FIG. 1. The sizes of the devices were identical to those of Example 1 except for the fluid taking-up portions.

Thereafter, glucose was incorporated at a concentration of 100 mg/dl into an aqueous solution of 5% by weight of albumin, and pH was adjusted to 7.6 to provide a pseudo-serum. This fluid was caused to drop on the skin of the subject, and the fluid taking-up device was attached to that part to carry out the fluid taking-up tests. The test was repeated fifteen times for the same part of the skin, and the glucose concentrations measured for respective tests were recorded. In the foregoing, the removal of the fluid which was once taken up into the fluid-passage member was effected by contacting the opening end of each fluid-passage member with cellulose, which is a water-absorbable material, to suck the same.

The standard deviations of the measured values for repeated tests over fifteen times for each device were divided by the average value and multiplied by 100. The results thus obtained were considered to exhibit reproducibility, and are set forth in Table 7.

TABLE 7

| Volumetric capacity of fluid-passage member ($\mu$m) | Reproducibility (%) |
| --- | --- |
| 2.5 | 2.9 |
| 5.0 | 2.2 |
| 7.5 | 2.9 |
| 10.0 | 3.1 |

The results shown in Table 7 show that it is possible to mount a sensor in the fluid-passage member, and that with respect to the measuring precision, a reproducibility of less than 5%, which is required for an abbreviated measurement in the clinical tests, can be achieved.

Obviously, many modifications and variations are possible in the light of the foregoing teachings. It is thus to be understood that within the scope of the appended claims, the invention may be practiced otherwise than as specifically described.

Finally, the present application claims the priority of Japanese Patent Application No. 9-021610 filed Feb. 4, 1997, which is herein incorporated by reference.

What is claimed is:

1. A device for taking up a fluid present on a flexible surface, comprising:

a support member including an opening portion having an end surface defining an abutment surface adapted to be held in abutment with the flexible surface, an exterior surface, and an opposing interior surface; and a fluid-passage member including an aperture, an exterior surface, and an opposing interior surface, said fluid passage member being disposed within said opening portion of said support member such that the exterior surface of said fluid passage member is interior to and spaced apart from the interior surface of said support member, said fluid-passage member including an opening end defining an inlet and being constructed to permit the fluid to flow thereinto by capillarity, said opening end having an end face being disposed inside with respect to said abutment surface of said support member and positioned such that, when said abutment surface of said support member is brought into abutment with the flexible surface, only the fluid present thereon is brought into contact with said end face.

2. The device as recited in claim 1, wherein said fluid-passage member comprises at least two of said openings.

3. The device as recited in claim 1, wherein said support member is constructed to permit the reduction of pressure within said opening portion.

4. The device as recited in claim 1, further comprising a pressure-reducing unit for reducing pressure within said opening portion of said support member when said opening portion of said support member is closed.

5. The device as recited in claim 1, further comprising a pressure-reducing unit detachably attached to said support member for reducing pressure within said opening portion of said support member when said opening portion of said support member is closed.

6. The device as recited in claim 1, further comprising a pressure-reducing unit for reducing pressure in said opening portion of said support member when said opening portion of said support member is closed, said pressure-reducing unit including a cylinder and a piston disposed in said cylinder.

7. The device as recited in claim 1, wherein said support member comprises a tubular structure having opposite opening ends, one of said opening ends defining said abutment surface.

8. The device as recited in claim 1, comprising a plurality of said fluid-passage members.

9. The device as recited in claim 1, wherein said support member comprises a tubular structure having opposite opening ends, and wherein said device comprises a pair of said fluid-passage members each associated with a respective one of said opposite opening ends.

10. The device as recited in claim 1, wherein said support member comprises a tubular structure having opposite opening ends, and wherein said device comprises a plurality of said fluid-passage members associated with each of said opposite opening ends.

11. The device as recited in claim 1, further comprising a sensor disposed in said fluid-passage member for detecting the fluid.

12. The device as recited in claim 1, wherein said fluid-passage member has an inner peripheral surface subjected to hydrophilic treatment.

13. The device as recited in claim 1, comprising said fluid-passage member attached releasably to said support member.

14. The device as recited in claim 1, wherein said flexible surface is an epithelium of an organism.

15. The device as recited in claim 1, wherein said flexible surface is the surface of skin.

16. The device as recited in claim 1, wherein the fluid present on the flexible surface is an aqueous fluid.

17. The device as recited in claim 16, wherein said aqueous fluid is a body fluid.

18. A device for taking up a fluid present on a flexible surface, comprising:

a support member including an opening portion having an end surface defining an abutment surface adapted to be held in abutment with the flexible surface; and a fluid-passage member including an aperture and disposed within said opening portion of said support member, said fluid-passage member including an opening end defining an inlet and being constructed to permit the fluid to flow therein by capillarity, said opening end having an end face being disposed inside with respect to said abutment surface of said support member and positioned such that, when said abutment surface of said support member is brought into abutment with the flexible surface, only the fluid present thereon is brought into contact with said end face, wherein said support member comprises a tubular structure having opposite opening ends, and wherein said device comprises a pair of said fluid-passage members each associated with a respective one of said opposite opening ends.

19. A device for taking up fluid present on a flexible surface, comprising:

a cylindrical support member with open first and second ends, said first end defining an abutment surface with the flexible surface; and a cylindrical fluid-passage member mounted in an interior of, and spaced from, said cylindrical support member and above a plane defined by said first end, said cylindrical fluid-passage member comprising a fluid inlet end adapted to accept fluid by capillarity.

* * * * *